(12) United States Patent
Carnali et al.

(10) Patent No.: US 10,322,076 B2
(45) Date of Patent: *Jun. 18, 2019

(54) COMPOSITION COMPRISING SALT OF ACYL GLUTAMATE AS PRIMARY SURFACTANT OR PRIMARY ANIONIC SURFACTANT

(71) Applicant: Conopco, Inc., Englewood Cliffs, NJ (US)

(72) Inventors: Joseph Oreste Carnali, Newtown, CT (US); Pravin Shah, Rutherford, NJ (US); Hongjie Liu, Livingston, NJ (US); Rajendra Mohanlal Dave, Newark, NJ (US)

(73) Assignee: CONOPCO, INC., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/526,845

(22) PCT Filed: Nov. 12, 2015

(86) PCT No.: PCT/EP2015/076478
§ 371 (c)(1),
(2) Date: May 15, 2017

(87) PCT Pub. No.: WO2016/079007
PCT Pub. Date: May 26, 2016

(65) Prior Publication Data
US 2017/0333320 A1    Nov. 23, 2017

(30) Foreign Application Priority Data
Nov. 18, 2014 (EP) .................................. 14193591

(51) Int. Cl.
*A61K 8/44* (2006.01)
*A61Q 5/02* (2006.01)
*A61Q 19/10* (2006.01)

(52) U.S. Cl.
CPC ............... *A61K 8/44* (2013.01); *A61Q 5/02* (2013.01); *A61Q 19/10* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 4,273,684 A | 6/1981 | Nagashima et al. | |
| 4,443,362 A * | 4/1984 | Guth | A61K 8/39 424/70.21 |
| 6,284,230 B1 * | 9/2001 | Sako | A61K 8/19 424/70.1 |
| 6,703,427 B2 | 3/2004 | Schmucker et al. | |
| 2004/0258807 A1 | 12/2004 | Pape et al. | |
| 2017/0333320 A1 | 11/2017 | Carnali et al. | |
| 2017/0333322 A1 | 11/2017 | Carnali et al. | |

FOREIGN PATENT DOCUMENTS

| | | |
|---|---|---|
| CN | 101199463 | 6/2008 |
| EP | 2402000 | 1/2012 |
| EP | 2532343 | 12/2012 |
| FR | 2995783 | 3/2014 |
| WO | WO2010069500 | 6/2010 |
| WO | WO2013045377 | 4/2013 |
| WO | WO2014146811 | 9/2014 |

OTHER PUBLICATIONS

IPRP2 in PCTEP2015076478, Jan. 26, 2017.
IPRP2 in PCTEP2015076479, Jan. 26, 2017.
IPRP2 in PCTEP2015076480, Jan. 27, 2017.
Search Report & Written Opinion in PCTEP2015076478, dated Dec. 23, 2015.
Search Report & Written Opinion in PCTEP2015076479, dated Apr. 15, 2016.
Search Report and Written Opinion in EP14193591, dated May 8, 2015.
Search Report and Written Opinion in EP14193684, dated May 19, 2015.
Search report and Written Opinion in PCTEP2015076480, dated Jan. 7, 2016.
Search Report in EP14193590, dated Apr. 24, 2015.
Written Opinion 2 in PCTEP2015076479, dated Oct. 14, 2016.
Written Opinion 2 in PCTEP2015076480, dated Oct 14, 2016.
Co-pending application for J9255USw; Carnali et al.
Co-pending application for J9256USw; Carnali et al.

* cited by examiner

Primary Examiner — Necholus Ogden, Jr.
(74) Attorney, Agent, or Firm — Foley & Lardner LLP

(57) ABSTRACT

The present invention relates to compositions which comprise salt of acyl glutamate as primary surfactant or primary anionic surfactant and which compositions are clear, low pH isotropic composition.

16 Claims, No Drawings

COMPOSITION COMPRISING SALT OF ACYL GLUTAMATE AS PRIMARY SURFACTANT OR PRIMARY ANIONIC SURFACTANT

FIELD OF THE INVENTION

The invention relates to personal care compositions. The compositions are preferably aqueous-based, isotropic, personal care compositions. The compositions are preferably mild (defined for example by low percent zein dissolved relative to harsher compositions). Preferably, the compositions have good foam volume (a signal of cleansing to many consumers) and are stable. Preferably, the compositions are clear at a pH of 6.5 and lower, preferably at 6.0 and lower (generally the pH of the composition may be from about 3 to 6.5). Preferably the pH is from about 3.5 to 6.0, more preferably from about 3.5 to 5.5, more preferably 4.0 to 5.5.

BACKGROUND OF THE INVENTION

Synthetic detergents, such as cationic, anionic, amphoteric, non-ionic surfactants, are widely used in personal care cleaning compositions. Anionic surfactants generally exhibit superior cleansing and foaming properties and are thus typically incorporated into such compositions. Anionic surfactants, however, also tend to be harsh on the skin.

Since consumers desire milder compositions (i.e., compositions which are not as harsh and irritating on skin and skin proteins), it is known to replace some anionic surfactant with other surfactants (e.g., nonionic and/or amphoteric surfactants). Another approach is to associate anionic surfactants with amphoteric or cationic compounds to create surfactant complexes (see U.S. Pat. No. 4,443,362). Often these compositions suffer in foaming and/or cleansing performance.

Another approach for providing mildness is to use milder anionic surfactants. Among such mild anionic surfactants that can be used are N-acylamino acids and their salts. The paper "Surface Active N-Acylglutamate: Preparation of Long Chain N-Acylglutamic Acid" (M. Takehaka et al.; Journal of the American Oil Chemists Society, Vol. 49, p. 157 ff) cites JP Patent No. 29444 (1964) according to which acyl glutamates are said to alleviate skin irritations caused by other anionic surfactants such as alkylbenzene sulfonates.

As seen in U.S. Pat. No. 6,703,427 to Schmucker et al., such acylamino acids are contemplated as co-surfactants to alleviate harshness of primary anionic surfactants. By themselves, as the primary surfactant (a "primary surfactant" is one which is present at a level of 50% or more of all surfactant) in a surfactant cleansing system (as is preferred for compositions of the invention), or as the primary anionic surfactant (as a "primary anionic surfactant", the surfactant is present at 50% or more of all anionic surfactants; however, surfactants other than anionic surfactants may in total comprise greater than 50% of the entire surfactant system or less than 50% of the system), such surfactant would be expected to be deficient in foam and/or cleansing relative to use of other anionic surfactants in the same composition. Further, acylamino acids are difficult to solubilize at lower pH ranges because the molecule will tend to precipitate. It would generally not be contemplated thus to use acylamino acids such as glutamate at a low pH and, typically, salt of glutamate does precipitate at about a pH of 5.5 and lower. As such, such glutamate salt molecules would not be contemplated for use in isotropic liquids (where solubility is required to ensure good clarity) at any significant level. In particular, they would not be contemplated for use as a primary surfactant, or as a primary anionic surfactant and where, simultaneously, the amount of glutamate is equal to or greater than, preferably greater than, any other single surfactant present. That is, according to our invention, if the salt of glutamate is primary anionic surfactant but the total sum of non-anionic surfactants is greater than that of anionic surfactant, the salt of glutamate must be present in an amount equal to or greater than any other surfactant present. It is preferred that the glutamate salt be present as the primary surfactant.

It would further not be contemplated to use acyl glutamate (unless specified otherwise, we use the term "glutamate" or "acyl glutamate" to mean the salt of the glutamate) as a primary surfactant or as a primary anionic surfactant (where glutamate is simultaneously present in an amount equal to or greater than any other single surfactant present), because glutamate does not structure (e.g., self-structure) as readily as other surfactants and therefore can make it more difficult to suspend particles and other benefit agents. As applicants have noted in a co-pending application, it is not readily apparent how to structure with external structurants while maintaining a relatively clear, isotropic liquid, particularly at a low pH (e.g., of 6.5 and lower, preferably 6.0 and lower). Applicants have filed a co-pending application relating to compositions where glutamate is the primary surfactant (and by definition the primary anionic surfactant) and in which specific structuring polymers are used to provide enhanced structuring of the liquids while maintaining desired clarity (at low pH of 6.5 and lower, preferably of 6.0 and lower, preferably of 4.0 to 6.0, more preferably 4.0 to 5.1).

In short, because acyl glutamate surfactants are not the type of anionic surfactants which provide superior foaming, because they do not readily solubilize (at lower pH), and because they do not self-structure as well as other anionics, such surfactants would not have been considered for use in a low pH (pH of 6.5 and lower) liquid cleansing composition as the primary surfactant; or as the primary anionic surfactant, but where the amount of glutamate is equal to or greater than any other single surfactant present. In particular, they would not be contemplated for use as primary or primary anionic surfactant in aqueous-based cleansing compositions while retaining the ability to maintain good stability and clarity values.

Unexpectedly, applicants have found that it is possible to formulate low pH, aqueous-based, isotropic compositions (which stay clear and stable) in which acyl glutamate is primary surfactant (preferred systems); or primary anionic surfactant and simultaneously present in an amount equal to or greater than any other single surfactant present. Preferably, the pH of the composition is 6.5 and lower. More preferably of pH is 3.5 to 6.0. More preferably, pH is 3.5 to 5.5 and most preferably 4.0 to 5.5, even more preferably 4.0 to 5.1. Preferably, the composition is visibly clear (isotropic). Preferably, the composition is a single phase (single phase which is isotropic), clear composition where clarity is defined by an absorbance value of 1.0 or lower, preferably 0.5 or lower (e.g., 0.01-0.5), more preferably 0.2 and below, when measured at wavelength of 550 nm.

Further, applicants have found that, when the amount of shorter chain glutamate (as a percent of all glutamate) is minimized (to ensure good foam) and the percent of glutamate relative to co-surfactant is maximized (saving on cost of use of co-surfactant while surprisingly maintaining low pH, clear, one phase isotropic compositions), preferred compositions are found. In preferred systems, glutamate is the primary surfactant (present at level of 50% or more, preferably 55% or more of all surfactant). Preferred systems comprising glutamate and particular co-surfactants are also disclosed.

In a co-pending application, applicants disclose compositions in which specific polymers can be used to further ensure that stable, isotropic liquids are formed at relatively low pH (pH of 6.5 and lower, preferably pH of 6.0 and lower, preferably pH of 5.5 and lower) also while maintaining defined level of clarity. Such stable and clear compositions would not be expected to form in systems where glutamate is the primary surfactant, or the primary anionic surfactant while simultaneously present in an amount equal to or greater than any other single surfactant present.

A variety of compositions have been disclosed where glutamate is disclosed broadly.

In U.S. Pat. No. 6,284,230 to Sako et al. a broad number of surfactants, including glutamates are said broadly to be able to be used as primary anionic surfactant. From the examples however, it is clear that where glutamate is used (Examples I-V), it is neither the primary surfactant (ammonium sulfate is in Examples I-V) nor is it the primary anionic surfactant. In Example VI, sarcosinate (different acyl amino acid with a single carboxylic acid group) is the primary surfactant. Never is an acyl amino acid having two carboxylic acid groups (such as glutamate) used as primary surfactant or as primary anionic surfactant in which the glutamate is used in an amount equal to or greater than any other single surfactant present.

US 2004/0258807 and US 2011/016506 are two other examples of references disclosing glutamates broadly but again it is clear that glutamates are never used as primary surfactants; or as primary anionic surfactant and where glutamate is simultaneously present in an amount equal to or greater than any other single surfactant present in the composition.

US 2005/034895 shampoo compositions comprise surfactant, microbiological control agent, rheological additive, conditioning agent and solubilizer. The surfactant compositions include mixtures of glutamate and other surfactants (see Examples 2-5), but glutamate is never primary surfactant or primary anionic where it is used in amounts equal to or greater than any other single surfactant in the composition.

WO 2010/069500 discloses in Example 1, Composition E, a composition having 3.5% glutamate, 3.5% sarcosinate, 8.5% betaine and 2.5% glucoside. In this composition glutamate is a primary anionic (it is present at level of 50% of anionic), but is not present in an amount equal to or greater than any other single surfactant present (e.g., betaine is single greatest surfactant present). It is also not the primary surfactant.

The present invention, as noted, requires the glutamate be either primary surfactant (preferred embodiment); or present as primary anionic surfactant while simultaneously being used in an amount equal to or greater than, preferably greater than, any other single surfactant present in the composition. For reasons noted above, formation of such system would not be contemplated because such systems where glutamate is used (especially as primary surfactant) in such relatively large amounts would have been thought to compromise the formation of compositions which are clear (isotropic), foam well, and are stable.

SUMMARY OF THE INVENTION

The present invention relates to compositions comprising:
1) 0.5-35% of a surfactant system wherein the anionic surfactant is present at 0.5 to 25%, preferably 1 to 15% by wt. of the total composition and where
   a) the salt of acyl glutamate is present at 50% or greater of all the surfactant present ("primary surfactant"); or
   b) is present at level of 50% or more of the anionic surfactant (preferably the salt of acyl glutamate comprises greater than 50% by wt. of the anionic, more preferably greater than 60% by wt. of total anionic) and simultaneously is present in an amount equal to or greater than any other single surfactant present in the composition ("primary anionic surfactant");
2) 0% to 20%, preferably 0.5 to 15% by wt. of a co-surfactant selected from the group consisting of nonionic, cationic and amphoteric surfactant and mixtures thereof (preferably, the co-surfactants comprise amphoteric surfactant, optionally further comprising nonionic; preferably amphoteric comprises 1-10% by wt. of total composition);
3) optionally, 0 to 30%, preferably 0.1-10%, more preferably 0.1-5% of a skin or hair benefit agent; and
4) balance water
   wherein pH is 6.5 and lower, preferably wherein pH is 6.0 and lower, more preferably, wherein pH is 5.5 and lower, more preferably where pH is 5.1 and lower.

A preferred pH range is about 3.5 to about 5.5, preferably 4.0 to 5.5, especially 4.0 to 5.1.

With regard to use of optional oil or emollient of component (3), applicants' first note that the invention may be defined as a surfactant chassis which itself is based on acyl glutamate as primary surfactant or primary anionic surfactant. The surfactant chassis is preferably a stable, single phase, isotropic, optically clear composition. However, when certain optional components (e.g., certain oils or emollients) are added to the surfactant chassis, these may not be completely miscible with the stable, isotropic, surfactant chassis and may render the resulting full formulation anisotropic (e.g., the composition is no longer "clear").

Thus, the invention may comprise a full formulation which contains no oil or emollient; or which contains a sufficiently low amount of oil or emollient; or which contains an oil or emollient which is miscible with the surfactant chassis so as not to become anisotropic as noted above. This formulation is a stable, single phase composition which is clear (isotropic) as defined by an absorbance value of 1.0 or lower at defined wavelength.

The compositions of the invention could preferably comprise immiscible benefit agent. The invention also comprises a full formulation which is anisotropic (not optically clear) but which is formed from the combination of (1) a stable, single phase surfactant chassis, which is preferably optically clear; and (2) optional ingredient(s) present in sufficient amount to render the final full formulation anisotropic. A final anisotropic formulation which is not formed from the stable, single phase, optically clear surfactant chassis is not considered part of the subject invention. Specifically, a composition which is anisotropic before addition of, for example, emollient or oil is not part of the invention.

Preferably, compositions of the invention (whether isotropic at full formulation or isotropic at chassis formation and anisotropic upon addition of certain benefit agents) are, or are formed from single phase isotropic systems. Preferably, the compositions (again, as final composition, or as isotropic chassis before addition of potential anisotropic forming benefits agents) maintain optical clarity. Preferably the compositions (as final isotropic composition or isotropic chassis) are single phase systems which maintain optical clarity as defined herein. Preferably the single phase, optically clear systems are stable and maintain a single, optically clear phase under ambient conditions (about 25° C.) over a period of one month or longer, preferably up to about one (1) year.

In typical, preferred compositions of the invention, the amount of glutamate surfactant is equal or is in excess of all other surfactants ("primary surfactant"); it may also be present at 50% or more of anionic and simultaneously in amount equal to or greater than any one other single surfactant ("primary anionic surfactant"). Even if the sum of surfactants other than anionic form more than 50% of the surfactant system, glutamate must be present in an amount equal to or greater than any other single surfactant. It is preferred, however, that glutamate be the primary surfactant. It is also preferred to maximize the amount of glutamate used and minimize use of cosurfactants.

Some compositions of the invention may contain 0 to 10% by wt., preferably 0.1 to 10% by wt., more preferably 0.5 to 7% by wt. of structurant. Such structurant may be water soluble or water dispersible polymer which can be a cationic, anionic, amphoteric or nonionic polymer for enhancing viscosity and stability of the cleanser and is selected from the group consisting of carbohydrate gums; modified and non-modified starch granules; polyacrylate and methacrylate polymer and copolymer; cationic polymers including cationic modified polysaccharide, cationic modified cellulose and synthetic cationic polymers. In applicants co-pending application, particular polymers are disclosed which define an enhanced stability benefit. As indicated, the structurant need not be present although it is preferred for stabilizing the composition and helping to suspend, especially to suspend oil soluble emollients. In a related co-pending application, applicants claim compositions comprising specific structurants which surprisingly maintain relatively clear (isotropic) liquids which are stable, all at defined low pH range.

Compositions of the invention may comprise water-soluble or oil-soluble skin or hair benefit agents. These may be present at levels of 0-30%, preferably 0.1-20% by wt., more preferably 0.1 to 10% by wt. total composition. Some compositions comprise water-soluble polyhydroxy alcohols. Preferred water soluble skin benefit agents include glycerin, sorbitol and polyalkylene glycols (a preferred polyalkylene glycol is polyethylene glycol) and mixtures thereof. Preferably, oil soluble emollients comprise 30% or less, preferably 10% or less, preferably 5% or less (e.g., 0.1 to 5% by wt.) of composition. In some preferred embodiments, oil soluble emollients or oils are absent.

In the absence of immiscible benefit agents (such as oil soluble emollient or oils), the final compositions are clear (isotropic). They may remain so if the quantities of immiscible ingredients are sufficiently small. However, even though the surfactant chassis is clear, the invention also contemplates full formulations which may be anisotropic but are formed from the combination of isotropic surfactant chassis and sufficient amounts of immiscible benefit agent to render the full formulation anisotropic.

DETAILED DESCRIPTION OF THE INVENTION

The invention relates to low pH cleansing compositions, preferably aqueous-based and clear, wherein salts of acyl glutamate are present as "primary surfactant"; or, where the glutamate salts are "primary anionic surfactants" (although non-anionic may be present at greater than 50% of all anionic surfactant) and are simultaneously present in an amount equal to or greater than any other single surfactant present. When glutamate is not present in an amount equal to or greater than any other single surfactant, such composition is not intended to be encompassed by compositions of the invention.

Whether or not the glutamate is primary surfactant, or primary anionic surfactant while simultaneously present in amounts equal to or greater than, preferably greater than any other single surfactant, it is seen that glutamate necessarily comprises 50% or greater of all anionic surfactant present and, as noted, is present in an amount equal to or greater than, preferably greater than, any other single surfactant in the composition. Because of the properties of glutamate noted above, it would not have been previously contemplated to form low pH compositions where glutamate is primary surfactant or primary anionic surfactant while maintaining stable, single phase, clear (isotropic) formulations. In some preferred compositions, the amount of short chain glutamate ($C_{10}$ or below) is minimized (to enhance foaming). In some preferred compositions, particular structurants are used to enhance structuring (while maintaining clarity), even at very low pH. These single phase, isotropically clear compositions are also preferably stable as defined above.

Although glutamate surfactants are milder than other anionic surfactants, they do not typically foam or cleanse as well. Like all acylamino surfactants, acyl glutamates are also difficult to solubilize at low pH and would therefore not be contemplated for use in low pH, clear (isotropic) compositions (i.e., lack of solubility would be believed to affect clarity), particularly at the relatively high levels of glutamate surfactant required in the subject invention. This is especially true for preferred systems where glutamate is the primary surfactant.

Unexpectedly, applicants have now produced low pH, stable, clear (isotropic) compositions (as final formulation or as surfactant chassis prior to addition of anisotropic inducing agents) wherein glutamate is the primary surfactant or primary anionic surfactant and present in an amount equal to or greater than any other single surfactant. Preferred compositions maximize the amount of glutamate used (as percent of total surfactant) in order to minimize costly co-surfactant. Further, preferred compositions minimize the amount of shorter chain length glutamate used and thereby enhance foaming. Finally, in other preferred compositions (as claimed in co-pending application), use of specific structurants allow use of maximum amounts of glutamate in clear, single-phase compositions (as final composition or as surfactant chassis) and particularly at low pH (e.g., of 5.5 and lower, preferably 5.0 and lower). In some preferred systems, the amount of benefit agent, particularly oil or oil soluble emollient, is minimized (0 to 30%, preferably 0 to 10%, preferably 0 to 5% by wt., preferably absent).

More specifically, compositions of the invention comprise:
1) 0.5 to 35% by wt. of total composition of a surfactant system (surfactant chassis) wherein the anionic surfactant is present at 0.5 to 25% by wt. of total composition and wherein salt of acyl glutamate
   a) is present at 50% or more, preferably 60% or more, more preferably 65% or more of all surfactant present ("primary surfactant"); or is present at 50% or more, preferably greater than 50%, more preferably greater than 60% of the anionic surfactant and is simultaneously present in amount equal to or greater than any other single (non-anionic) surfactant in the composition ("primary anionic surfactant"); for purposes of this definition, if the glutamate and the second anionic surfactant both comprise 50%, glutamate is still considered a "primary anionic surfactant"; and b) 0% to 20%, preferably 0 to 15% by wt. of a co-surfactant selected from the group consisting of nonionic, cationic and amphoteric surfactants and mixtures thereof; preferably there is present amphoteric surfactant as 1-10% by wt. of total composition. By co-surfactant is meant surfactant separate from the glutamate and separate from any additional anionic surfactant which defines component (a) above (i.e., although other anionic surfactants comprise part of component (a) and are used in amount 50% or less of total anionic, component (b) is concerned with surfactants which are not anionic);

Depending on particular co-surfactants used (and to some extent the chain length of glutamate salts), the amount needed to optimize in a system with glutamate and amphoacetate, the amount of amphoacetate to glutamate required to maximize isotropic region can be in ratio of 1/7 (using mix of decanoyl and cocoyl glutamate) (e.g., 12.5% amphoacetate to 87.5% glutamate; see Table 2) and higher or even 1/1.7 (even more amphoacetate; using mix of decanoyl and lauroyl, see Table 1) and higher (up to 1/1); by contrast when using CAPHS or cocoyl betaine, less co-surfactant can be used (e.g., ratio of 1/19 and higher, see Tables 4 and 5 where stable regions are obtained at about 5% CAPHS or cocoylbetaine to 95% glutamate) while maximizing isotropic region.

The above are non-limiting examples of some co-surfactants which may be used and, as noted, are not intended to limit the invention in any way.

2) optionally 0 to 30%, preferably 0.1 to 20%, more preferably 0.1 to 10% by wt. of a skin or hair benefit agent; preferably the benefit agent is an oil-soluble emollient or moisturizing oil (although water-soluble agents may also be used). Preferably it is petrolatum or silicone. Also preferably, the oil is a vegetable or triglyceride oil. Preferred oils include sunflower seed oil and soybean oil. Other oils are noted below. Preferably the emollient can be an ester of long chain (e.g., 014-030) fatty acid such as isopropyl palmitate or cetyl lactate; combinations of any of the above are preferred; and 3) balance water and other ingredients as defined below wherein pH of composition is 6.5 and below, preferably 6.0 and below, more preferably 5.5 and below; preferably pH is 3.5 to 6.0, more preferably 3.5 to 5.5, more preferably 4.0 to 5.5.

As indicated, the amount of glutamate may be such that it is the primary surfactant overall; or glutamate may be the primary anionic surfactant, while the amount of surfactants other than anionic is in excess of the glutamate. Where glutamate is the "primary anionic surfactant", but the surfactant system has less than 50% anionic surfactant overall, glutamate must be present in amount equal to or greater than any other single surfactant present in the composition.

Further, the compositions of the invention are clear (isotropic) one-phase solutions. That is, there is one single clear phase (rather than one phase which is clear as part of a multi-phase solution). The phase is stable (does not break into multi-phases). By clear is meant having absorbance value of 1.0 or lower, preferably 0.5 or lower, more preferably 0.2 and below when measured at wavelength of 550 nm.

If benefit agent component (2) is not completely miscible in the surfactant chassis of (1), the composition may be anisotropic. However, the invention is defined either by presence of component (2) which is miscible so that final formulation is isotropic or, by final anisotropic composition which was formed from combination of isotropic chassis of component (1) and benefit agent of component (2). The key to invention, however, is formation of final composition (isotropic; or anisotropic from an isotropic chassis defined by components (1) and (3)) having a pH and stability, as well as clear, one-phase isotropic characteristics defined.

Surfactant System

Anionic Surfactant

A key to the invention is that there is present 0.5 to 35% by wt. of total composition of a surfactant system wherein anionic surfactant comprises 0.5 to 25% by wt. of total composition and wherein salt of acyl glutamate comprises 50% or more of all surfactant ("primary surfactant"); or 50% or more, preferably 60% or more by wt. of the total anionic surfactant present (even if anionic overall is less than 50% of total surfactant), and is present in an amount equal to or greater than any other single surfactant in the composition. Preferably anionic surfactant comprises 1-15% by wt. of total composition, more preferably 2 to 12% of total composition. In some compositions, anionic comprises 5-12% by wt. of the total composition and surfactants which are not anionic comprise 1 to 7% by wt. of the composition. The amount of glutamate should always be maximized and as noted, even if other surfactants are present in amounts greater than anionic (e.g., when glutamate is not the "primary surfactant"), glutamate is present at 50% or more of anionic surfactant and is present in an amount equal to or greater than any other single surfactant present.

The salt of acyl glutamate used in the composition of this invention has a structure as follows:

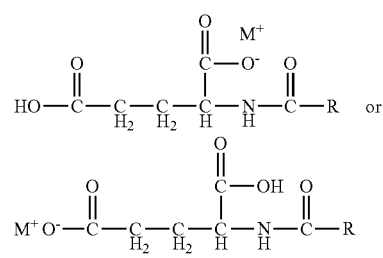

(It is noted that one or the other structures will occur at pH levels of the invention (pH 6.5 and below, preferably 3 to 6.5) and that at higher pH (e.g., 8 or 9), some di-salt is also present), where R is alkyl or alkenyl group (generally saturated although some unsaturated, for example, oleoyl, may be present) having 8 to 20 carbons, preferably 8 to 16 carbons, more preferably 10 to 14 carbons. Preferably, R is predominantly a mixture of $C_{10}$ to $C_{14}$. As indicated above, for preferred levels of foaming, it is preferable to minimize the amount of shorter chain length (e.g., $C_8$ and $C_{10}$) and to maximize longer chain length, e.g., $C_{12}$-$C_{20}$, preferably $C_{12}$-$C_{18}$. Although $C_{10}$ should be minimized, it will be seen, at least in some embodiments of the invention, that ratio of $C_{10}$ to $C_{12}$ should be at least 1/5, possibly 1/3 and higher (in part depending on co-surfactant used with glutamate salts) to ensure isotropic formation. Preferably ratio should be no higher than 1 to 1, regardless of the co-surfactant used (if any) with glutamate salts.

As used in the examples, a cocoyl chain length distribution is typically defined as follows: 13% $C_8$-$C_{10}$, 50% $C_{12}$, 18% $C_{14}$, 8% $C_{16}$, and 11% $\geq C_{18}$, (http://coconutboard.nic.in/English-Article-Gopalakrishna-CFTRI.pdf), as preferred here.

M is a solubilizing cation such as, for example, sodium, potassium, ammonium or substituted ammonium. It is preferred that the cation is sodium or potassium, more preferably sodium. Sodium salt is preferred.

The pH of the overall composition is typically 6.5 and lower, preferably 6.0 and lower. Preferably pH is 3 to 6.5 and more preferably 3 to 6. More preferably, pH is 3.5 to less than 6, preferably 3.5 to 5.5, more preferably 4.0 to 5.5, even more preferably 4.0 to 5.1.

The pKa of the salt of acyl glutamate is relatively low (about 5). Applicants have surprisingly found that the relatively large amounts of glutamate used can be solubilized thereby allowing to take advantage of the mildness of this anionic surfactant relative to other anionic surfactants.

Further, surprisingly large amounts of glutamate can be solubilized at low pH, thereby permitting formation of clear, one-phase isotropic compositions which are also mild.

Clear and mild cleansers are seen as highly desirable by consumers. By clarity, applicants mean having absorbance value of 1.0 or lower, preferably 0.5 or lower, even more preferably 0.2 or lower when measured at wavelength of 550 nm. As indicated above, clarity values define the surfactant chassis and water. Composition may maintain clarity (stay isotropic) upon addition of benefit agent but, even if final composition is anisotropic, if the initial chassis was isotropic as defined, it falls within definition of the invention.

While the acyl glutamate salt may be used as the only anionic surfactant in the total composition, it is desirable to use other anionic surfactants, subject to the levels defined here. One preferred co-anionic (as opposed to co-surfactant 1(b)) is sarcosinate (alkyl salt of $C_{10}$-$C_{14}$ acyl sarcosinate is a preferred sarcosinate, where salt is defined as in M above). Another preferred co-anionic is a taurate. A salt of $C_{10}$-$C_{14}$ acyl taurates (e.g., sodium cocoyl methyl taurates) is preferred. Generally, it is preferred not to use salts which would tend to precipitate at lower pH values. Thus, it is preferred to minimize, for example, the amount of acyl glycinate (<1.0%, preferably <0.5%, preferably absent altogether).

Generally, sarcosinate have formula:

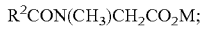
$R^2CON(CH_3)CH_2CO_2M$;

Taurates have formula:

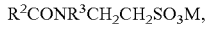
$R^2CONR^3CH_2CH_2SO_3M$, where $R^3$ is methyl;
Glycinates have formula:

$R^2CONHCH_2CO_2M$ where $R^2$ above is alkyl or alkenyl having 8 to 22 carbons, preferably 12 to 18 carbons; and M is solubilizing cation as defined above.

Compositions of the invention may have low levels of alkyl ether sulfates, for example, sodium lauryl ether sulfate. By low is meant <20% of anionic, preferably <10%, more preferably <5%. In some embodiments the compositions have <0.5% alkyl ether sulfate and in some there is substantially no alkyl ether sulfate. These types of sulfates are preferably minimized because they are less mild than other surfactants.

Co-Surfactant

A second component of the invention may comprise 0% to 20%, preferably 0.5 to 15% by wt. of total composition of a co-surfactant selected from the group consisting of nonionic, cationic, and amphoteric surfactant and mixtures thereof.

Preferred co-surfactants are amphoteric or zwitterionic surfactant. Preferably the co-surfactant is amphoteric.

This general class of amphoteric detergents has the following general structure:

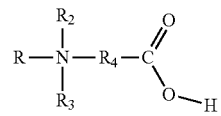

where R is an alkyl or alkenyl radical of 7 to 17 carbons or a carboxamido functional group of the general structure

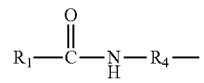

where $R_1$ is an alkyl or alkenyl radical of 7 to 17 carbons and $R_4$ is an alkyl, hydroxyalkyl, or carboxyalkyl radical of 1 to 3 carbons. $R_2$ and $R_3$ are each independently a proton, an alkyl, hydroxyalkyl, or carboxyalkyl radical of 1 to 3 carbons, or is missing entirely, subject to the following restraints. When $R_2$ and $R_3$ are each independently an alkyl, hydroxyalkyl, or carboxyalkyl radical, the nitrogen in a quaternary amine and is a cationic charge center. When one of $R_2$ or $R_3$ is an alkyl, hydroxyalkyl, or carboxyalkyl radical and the other is a proton or is missing entirely, the nitrogen is a tertiary amine. At a pH well below the pKa of the tertiary amine, the other of $R_2$ or $R_3$ will be a proton and the amine will be a cationic charge center. At a pH well above the $pK_a$ of the tertiary amine, the other of $R_2$ or $R_3$ will be missing entirely and the amine will be a neutral charge center.

Preferred examples of amphoteric noted above include cocoamidopropylbetaine (CAPB), $C_{10}$-$C_{14}$ alkyl betaine, the salt of $C_{10}$-$C_{14}$ alkyl amphoacetate (e.g. lauroamphoacetate) and mixtures thereof.

Another class of amphoteric detergents are the sultaines having the following general structure:

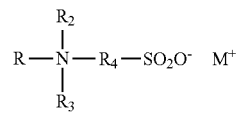

where R is an alkyl or alkenyl radical of 7 to 17 carbons or a carboxamido functional group of the general structure

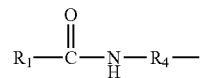

where $R_1$ is an alkyl or alkenyl radical of 7 to 17 carbons and $R_4$ is an alkyl, hydroxyalkyl, or carboxyalkyl radical of 1 to 3 carbons. $R_2$ and $R_3$ are each independently an alkyl, hydroxyalkyl, or carboxyalkyl radical of 1 to 3 carbons, so that the nitrogen in a quaternary amine and is a cationic charge center. A preferred amphoteric surfactant of this class is cocamidopropyl hydroxy sultaine (CAPHS), lauramidopropyl hydroxy sultaine (LAPHS), or lauryl hydroxy sultaine (LHS).

A preferred combination of the invention is salt of glutamate and salt of sarcosinate as anionic surfactants in combination with salt of amphoacetate (preferably $C_{10}$-$C_{14}$ amphoacetate) as co-surfactant. A preferred combination comprises 3-8% by wt. total composition salt of glutamate, 1-3% by wt. total composition salt of sarcosinate (where, preferably, glutamate is the primary surfactant or primary anionic as defined above) and 3-8% by wt. total composition salt of amphoacetate (particularly alkali metal salt of acyl amphoacetate). As previously noted, glutamate must be present in an amount equal to or greater than any other single surfactant present.

A key aspect of compositions of the invention is that (as full isotropic composition, or as surfactant chassis prior to forming composition) they are stable, clear, one-phase isotropic liquids, particularly at pH values of 6.5 and lower, preferably pH of 3.5 to 6.0, more preferably 3.5 to 5.5, more preferably 4.0 to 5.5.

The glutamate salts may comprise a mixture of chain lengths. As indicated, it is typically preferably to minimize shorter $C_8$ and $C_{10}$ lengths as these do not typically foam as well. Using a mixture of $C_{10}$ and cocoyl also helps to extend regions of isotropic clarity compared to mixtures where only, for example, $C_{10}$ and $C_{12}$ are used. This suggests that some amount of $C_{14}$ to $C_{20}$ may also be preferred.

In some compositions, the surfactant system comprises a mixture of $C_{10}$ and cocoyl glutamate together with alkali metal salts of amphoacetate.

Primarily, the invention is about the unexpected observation that glutamate may be used as primary surfactant; or as primary anionic surfactant and is simultaneously used in an amount equal to or greater than any other single surfactant present in the composition. Preferably it is used as primary surfactant in low pH, aqueous-based single-phase, compositions having visual clarity. Even if added benefit agent causes formation of final anisotropic composition, the surfactant chassis, prior to addition of anisotropic forming agent, is isotropic. Because of their low pH solubility, it is thus possible to make a mild composition (acylamino surfactant being mild) which is also optically clear (isotropic). At the same time, because these are low pH compositions, they can provide antibacterial effect while avoiding use of certain antibacterial agents which are restricted in certain parts of the world.

Thus, anisotropic compositions (formed using glutamate-based isotropic chassis) with low pH and low pH compatible preservation systems are another aspect of the invention.

Use of these milder glutamate surfactants at relatively high levels also permits that lesser amounts of cosurfactants (e.g., amphoacetate, CAPB) be used. It can be seen that amphoacetate maintains a wider isotropic region than CAPB (Tables 1 & 2 versus Table 3). Similarly CAPHS and coco betaine maintain a wider isotropic region than CAPB (Tables 4 and 5 versus 3). This is important in particular for fully formulated isotropic compositions.

When a mixture of $C_{10}$ and $C_{coco}$ is used (see e.g. Table 2), which can be preferred in this invention, compared to mixture of $C_{10}$ and $C_{12}$ (Table 1) an isotropic region is achieved using lower amounts of $C_{10}$ glutamate. That is, less $C_{10}$ is needed to achieve soluble region (which also helps with lather production). Systems with glutamate plus amphoteric co-surfactant are hence preferred (e.g., amphoacetate or cocoamidopropylbetaine). Non-ionic surfactant is a preferred additional co-surfactant in a glutamate/co-surfactant system.

Our examples show that changing the distribution of the chain length on the glutamate surfactant can also provide preferred isotropic compositions. Thus, as use of glutamate is enhanced and the amount of cosurfactant minimized, the amount of lower chain length (e.g., $C_8$, $C_{10}$) glutamate can be lessened while still obtaining clear isotropic compositions at low pH. Using more of the higher chain length glutamate (e.g., $C_{12}$ to $C_{20}$) also helps maintain good foam values.

As indicated above, while $C_{10}$ should be minimized, depending on specific surfactant systems, in some embodiments of the invention ratio of $C_{10}$ to $C_{12}$ should be at least 1/5, possibly 1/3 and higher (although preferably no higher than 1/1) to ensure formation of isotropic compositions as defined.

Preferred stable, isotropic compositions are those with a ratio of $C_{10}/C_{12}$ acyl glutamate of about 1/3 and higher and with a ratio of lauroamphoacetate/acyl glutamate of about 1/1.7 and higher (up to 1/1). To ensure good foam performance and minimize costs, the ratio of $C_{10}/C_{12}$ acyl glutamate is preferably 1/1 and lower (preferably above 1/3) and the ratio of lauroamphoacetate/acyl glutamate should be 1/1 or lower.

There is thus the desired benefit achieved of preferred compositions with enhanced glutamate (using less cosurfactant) and greater amounts of higher chain glutamate (better foaming, especially good since there is less co-surfactant). Again, enhanced foam benefit from compositions based on isotropic surfactant chassis is seen whether final formulations are isotropic or anisotropic.

Preferably, the glutamates should be used in a concentration of ≥50% of surfactant system, more preferably ≥60%, more preferably >70%.

One composition which can be used comprises 50% glutamate and alkali metal alkyl ($C_8$-$C_{14}$) amphoacetate, preferably lauroamphoacetate. The composition may comprise a mixture of $C_{10}$ and $C_{12}$ or $C_{10}$ and $C_{coco}$ glutamate ($C_{coco}$ glutamate is glutamate with cocoyl chain length distribution as defined above). Mixtures of $C_{10}$ and $C_{coco}$ are preferred if it is desired to minimize $C_{10}$ content since higher chain lengths typically provide better foaming. Such a mixture of $C_{10}$ and $C_{coco}$ preferably has a $C_8$-$C_{10}$ chain length distribution wherein $C_8$-$C_{10}$ is present in an amount of more than 13%, preferably more than 15% of all R groups on glutamate salt as defined above.

In addition to absolute amounts of co-surfactant (preferred to minimize), in some specific compositions we can define approximate minimum ratios of co-surfactant to glutamate needed to ensure isotropic formation. Thus, in amphoacetate/glutamate systems, the ratio of amphoacetate to glutamate is preferably about 1/7 and higher (up to 1/1) to maximize isotropic region. This may depend on chain lengths of glutamate and another preferred system is where mix of decanoyl and lauroyl glutamate is used and ratio of amphoacetate to glutamate is 1 to 1.7 and higher (preferably glutamate is primary surfactant overall).

Preferred stable, isotropic compositions are those with a ratio of $C_{10}/C_{coco}$ acyl glutamate of about 1/3 and higher and with a ratio of lauroamphoacetate/acyl glutamate of about 1/7 and higher. To ensure good foam performance, minimize costs, and observe an enhanced viscosity, the ratio of $C_{10}/C_{coco}$ acyl glutamate is preferably 1/1 and lower (preferably about 1/3 and above) and the ratio of lauroamphoacetate/acyl glutamate should be 1/1.7 or lower.

Another composition that may be used (although not preferred) comprises 50% glutamate and betaine, for example, cocoamidopropyl betaine. In such systems, glutamate comprises ≥60% of the surfactant system, more preferably 75%, more preferably ≥80%. In a preferred system of the invention the ratio of amphoacetate to glutamate can be 1/19 and higher (preferably glutamate is primary surfactant). In such system, less co-surfactant is required to optimize isotropic region (e.g., compared to use of cocamidopropylbetaine).

Similarly, another preferred embodiment comprises a surfactant system which is a mix of CAPHS and glutamate and where ratio of CAPHS to glutamate salts is as low as 1/19 and higher (up to 1/1). Again, it is seen that less co-surfactant is needed to optimize isotropic region compared to CAPB.

Generally, preferred compositions are those in which salt of glutamate is selected from the group consisting of C10, C12 and $C_{coco}$ glutamate and mixtures thereof. In a mixture comprising $C_{coco}$, mixture preferably has a $C_8$-$C_{10}$ chain length distribution wherein $C_8$-$C_{10}$ is present in an amount of more than 13%, based on all R chain lengths on the glutamate salts. In such general composition, preferably amphoacetate is co-surfactant and preferably the ratio of amphoacetate to glutamate is 1/7 and higher, preferably 1/7 to 1/1. Another preferred co-surfactant is one selected from the group consisting of betaine, sultaine and mixtures thereof wherein the ratio of co-surfactant to glutamate is 1/19 and higher, preferably 1/19 to 1/1

Preferred stable, isotropic compositions are those with a ratio of $C_{10}$/$C_{coco}$ acyl glutamate (using CAPHS, less co-surfactant is needed to obtain isotropic region compared to certain other co-surfactants, e.g., CAPB or amphoacetate) of about 1/7 and higher and with a ratio of CAPHS/acyl glutamate of about 1/19 and higher. To ensure good foam performance, minimize costs, and observe an enhanced viscosity, the ratio of $C_{10}$/$C_{coco}$ acyl glutamate is preferably 1/1 and lower and the ratio of CAPHS/acyl glutamate is preferably 1/1 or lower.

Skin or Hair Benefit Agents

In the same composition of the invention, 0 to 30% by wt., preferably 0.1 to 10%, more preferably 0.1 to 5% by wt. skin or hair benefit agent is used. As the skilled person will understand, in the present composition, the benefit agent is a different compound than the surfactants indicated under the surfactant system. Hence, preferably, the benefit agent preferably is not a surfactant. Preferably the benefit agent is an oil soluble emollient or moisturizing oil. These are molecules which increase hydration by various mechanisms which may include prevention of water loss (occlusive agents), attracting moisture (humectants); or which restore natural moisturizing factors to the skin (e.g., amino-lipids). Preferred moisturizers include petrolatum and silicone. Preferably, moisturizer is a vegetable or triglyceride oil. Preferred oils include sunflower seed oil and soybean oil. The moisturizer may be an ester of long chain [$C_{14}$-$C_{30}$] fatty acid, such as isopropyl palmitate.

Some naturally restorative agents and moisturizers include:
  a) vitamins such as vitamin A and E, and vitamin alkyl esters such as vitamin C alkyl esters;
  b) lipids such as cholesterol, cholesterol esters, lanolin, sucrose esters, and pseudo-ceramides;
  c) liposome forming materials such as phospholipids, and suitable amphiphilic molecules having two long hydrocarbon chains;
  d) essential fatty acids, poly unsaturated fatty acids, and sources of these materials;
  e) triglycerides of unsaturated fatty acids such as sunflower oil, primrose oil, avocado oil, almond oil;
  f) vegetable butters formed from mixtures of saturated and unsaturated fatty acids such as Shea butter;
  g) minerals such as sources of zinc, magnesium and iron; and
  h) silicone oils, gums, modifications thereof such as linear and cyclic polydimethylsiloxanes, amino, alkyl and alkyl aryl silicone oil.

Water soluble benefit agents may also be used. Preferred water-soluble agents include glycerin, sorbitol, polyalkylene glycols and mixtures thereof.

If used, depending on amount and miscibility of benefit agent in the isotropic surfactant chassis, the chassis may still maintain clarity. However, even if benefit agent renders chassis anisotropic, the low pH and foaming benefits discussed above are still retained.

Although compositions of the invention do not require external structurants, when oil soluble benefits as noted above are used, it is preferably to use structurants.

Structurant

Preferably, compositions of the invention comprise 0.1 to 10% by wt., preferably 0.5 to 7% by wt. of a structurant. The structurant may be a water soluble or water dispersible polymer which can be a cationic, anionic, amphoteric or nonionic polymer for enhancing viscosity.

Examples of water soluble/or dispersible polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum traganth, gum Arabic, gum acavia, gum agar, xanthan gum and mixture thereof; modified and non-modified starch granules with gelatinization temperature between 30 to 85° C., and pregelatinized cold water soluble starch; polyacrylate; Carbopols; alkaline soluble emulsions polymer such as Aculyn 28, Aculyn 22 or Carbopol Aqua SF1; cationic polymers such as modified polysaccharides including cationic guar available from Rhone Poulenc under the trade name Jaguar C13S, Jaguar C14S, Jaguar C17, or Jaguar C16, BF Guar C17 from Lamberti, Aqua D4091 or Aqua D4051 from Aqualon; cationic modified cellulose such as UCARE Polymer JR30 or JR 40 from Amerchol; N-Hance 3000, N-Hance 3196, N-Hance CPX215 or N-Hance GPX 196 from Hercules; synthetic cationic polymer such as Merquat 100, Merquat 280, Merquat 281 and Merquat 550 by Nalco; cationic starches, e.g., StaLok® 100, 200, 300 and 400 made by Staley Inc.; cationic galactamannans based on guar gum of Galactasol 800 series by Henkel, Inc.; Quadrisect Um-200, and Polyquaternium-24.

Gel forming polymers such as modified or non-modified starch granules, xanthan gum, Carbopol, alkaline-soluble emulsion polymers and cationic guar gum such as Lamberti BF Guar 017, and cationic modified cellulose such as UCARE Polymer JR 30® or JR 40® are particularly preferred for this invention.

A preferred structuring copolymer is the polymerization product (e.g., additive polymerization product) of (1) a first ethylenically unsaturated monomer; (2) a second ethylenically unsaturated monomer; (3) (meth)acrylate monomer and (4) associative monomer (generally random in structure; preferably copolymers are linear).

The first monomer of (1) may be di-acid of formula:

$$HOOC—CR^1=CR^2—OOOH \quad (I),$$

a cyclic anhydride precursor of diacid (I), the anhydride having the formula:

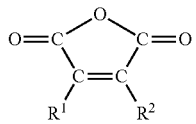

(II)

and combinations thereof,
wherein $R^1$ and $R^2$ are individually selected from H, $C_1$-$C_3$ alkyl, phenyl, chlorine and bromine and, in one or more embodiments, are preferably individually selected from H and $C_1$-$C_3$ alkyl.

Preferred monomers include maleic acid and maleic acid anhydride. It may comprise 0 to 10%, preferably 0.1 to 5% by wt. on total wt. of monomer charge.

The second monomer (2) can be acrylic acid, methacrylic acid and combinations thereof. It can be used at 15-60% by wt. based on total monomer charges.

The third (meth)acrylate monomer can be $C_1$ to $C_8$ alkyl esters of acrylic acid, $C_1$ to $C_8$ alkyl alkyl esters of methacrylic acid and combinations and can be 30-75% by wt. based on total monomer charge.

a) The associative monomer has the formula:

$$R^4—CH=C(R^3)—C(O)—O—(R^5O)_a—R^6 \quad (III)$$

wherein:
$R^3$ and $R^4$ are independently selected from H and $C_{1-3}$ alkyl,
each $R^5O$ is independently an oxyalkylene unit having from 2 to 4, preferably from 2 to 3 carbon atoms,
$R^6$ is selected from:
  linear and branched alkyl having from 8 to 40, preferably from 8 to 30, more preferably from 10 to 22 carbon atoms, and
  alkaryl, the alkyl group of which has from 8 to 40, preferably from 8 to 30, more preferably from 10 to 22 carbon atoms, such alkyl group being linear or branched, said alkaryl preferably being alkylphenyl; and
a has a value of from 6 to 40, preferably from 15 to 35, most preferably from 20 to 30.

Of particular interest in one or more embodiments is an associative monomer of the formula:

$$CH_3[CH_2]_b—CH_2—[OCH_2CH_2]_a—O—C(O)C(R^3)=CH(R^4) \quad (IV)$$

in which $R^3$, $R^4$ and a are as described above, and b has a value of from 6 to 38, preferably from 6 to 28, and more preferably from 8 to 20.

In the Formula III and Formula IV monomers, $R^3$ is preferably a methyl group and $R^4$ is preferably H. In the above described associative monomers, a and b represent the number of their respective oxyalkylene and —$CH_2$— repeat units and generally are integers. In one or more embodiments of interest a is greater than or equal to b.

The associative monomer may be employed in amounts of from 1 to about 25 wt. %, preferably from 2 to 20 wt. %, and more preferably from 2 to 15 wt. %, based on total monomer added. In one or more embodiments of particular interest the amount of associative monomer employed is from 5 to 12 wt. %, based on total monomer added.

In some compositions a structurant which has been found particularly effective to maintain clarity and stability is copolymer of the following formula:

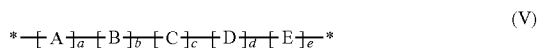

(V)

wherein a, b, c, d and e represent the percentage by weight that each repeating unit monomer is contained within the copolymer;
A is a polyacidic vinyl monomer selected from the group consisting of maleic, fumaric, itaconic, citraconic and acid combinations thereof and anhydrides and salts thereof; and
B is acrylic or methacrylic acid or a salt thereof;
C is a $C_1$-$C_8$ ester of acrylic acid or methacrylic acid;
D is an associative monomer of formula (VI)

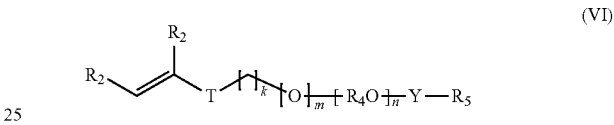

(VI)

wherein each $R_2$ is independently H, methyl, —C(=O)OH, or —C(=O)$OR_3$;
$R_3$ is a $C_1$-$C_{30}$ alkyl;
T is —$CH_2$C(=O)O—, —C(=O)O—, —O—, —$CH_2$O—, —NHC(=O)NH—, —C(=O)NH—, —Ar—$(CE_2)_z$-NHC(=O)O—, —Ar—$(CE_2)_z$-NHC(=O)NH—, or —$CH_2CH_2$NHC(=O)—;
Ar is divalent aryl;
E is H or methyl;
z is 0 or 1;
k is an integer in the range of 0 to 30; and m is 0 or 1; with the proviso that when k is 0, m is 0, and when k is in the range of 1 to 30; m is 1;
$(R_4O)_n$ is polyoxyalkylene, which is a homopolymer, a random copolymer, or a block copolymer of $C_2$-$C_4$-oxyalkylene units, wherein $R_4$ is $C_2H_4$, $C_3H_6$, $C_4H_8$, or a mixture thereof, and n is an integer in the range of 5 to 250;
Y is —$R_4$O—, —$R_4$H—, —C(=O)—, —C(=O)NH—, $R_4$NHC(=O)NH—, or —C(=O)NHC(=O)—; and
$R_5$ is substituted or unsubstituted alkyl selected from the group consisting of $C_8$-$C_{40}$ linear alkyl, $C_8$-$C_{40}$ branched alkyl, $C_8$-$C_{40}$ carbocyclic alkyl, $C_2$-$C_{40}$ alkyl-substituted, phenyl, aryl-substituted $C_2$-$C_{40}$ alkyl, and $C_8$-$C_{80}$ complex ester; wherein the $R_5$ alkyl group optionally comprises one or more substituents selected from the group consisting of hydroxy, alkoxy, and halogen; and
E when present is a cross linking monomer for introducing branching controlling molecular weight, the cross linking monomer comprising poly functional units carrying multiple reactive functionalization groups selected from the group consisting of vinyl, allylic and functional mixtures thereof, the groups A, B, C, D and E being covalently bonded one to another in a manner selected from a random, a block or a cross-linked copolymer format.

Amounts of "a" may range from about 0 to 10%, preferably 0.1 to about 5% by weight; amounts of "b" may range from about 10 to about 80%, preferably 15 to 60% by weight; amounts of "c" may range from about 30 to about 85%, preferably 30 to 75% by weight; amounts of "d" may range from about 1 to about 25% by weight; and amounts of "e" may range from 0 to about 5% by weight of the total copolymer.

Some compositions may contain water-soluble polymers in amounts of 0.005 to 5% by wt.

Examples of water soluble polymers include high molecular weight polyethylene glycols such as Polyox® WSR-205 (PEG 14M), Polyox® WSR-N-60K (PEG 45M), and Polyox® WSR-301 (PEG 90M); the carbohydrate gums such as cellulose gum. Hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, and xanthan gum; modified starch granules and pregelatinized cold water soluble starch; cationic polymer such as modified polysaccharides including cationic guar available from Rhodia under the trade name Jaguar®; cationic modified cellulose such as UCARE Polymer JR 30 or JR 40 from Amerchol; N-Hance® 3000, N-Hance® 3196, N-Hance® GPX 215 or N-Hance® GPX 196 from Hercules; synthetic cationic polymers such as Merquat® 100, Merquat® 280, Merquat® 281 and Merquat® 550 sold by Nalco. The water soluble polymers may be used individually or as combinations of two or more polymers from the same or different classes. High molecular weight polyethylene glycols Polyox® WSR-301 (PEG 90M) and Polyox® WSR-N-60K (PEG 45M) and guar derivatives such as Jaguar® S, Jaguar® C17, and Jaguar® C13, and synthetic cationic polymers such as Merquat® 100 are particularly desired.

Preservatives

Personal product formulations provide good media for growth of microbes. Microbial action can be manifested in terms of hydrolysis, oxidation or reduction and may cause off-odors, changes in color, adverse change in pH, breaking of emulsions, and changes in product texture. Thus good preservation systems are required to prevent microbial growth, spoiling of product, and infection of skin and hair. The preservative should be effective against Gram-negative and Gram-positive bacteria as well as fungi (molds and yeasts).

An effective preservative is a chemical agent which will prevent microbial growth in the product, making it safe and increasing shelf life.

Optimal preservation system should provide broad spectrum activity and be effective over the shelf-life of the product. As microorganisms multiply in the aqueous phase of formulations, it should also be water-soluble. Where formulations contain appreciable levels of oils, the system should favor partitioning into the aqueous phase. Ideally, the preservation system should be effective over wide pH range, colorless and safe in use. It should be non-irritating, non-sensitizing and preferably non-poisonous. Ideally, while eliminating pathogenic organisms in the formulation while in storage, it should leave symbiotic organisms on the skin in peace after application of the formulation to the skin, hair or mucous membrane.

Some preferred preservatives include:
1) Parabens, for example, methyl-, ethyl-, propyl-, isobutyl-, and butyl-paraben;
2) Formaldehyde-releasing preservatives, for example, formaldehyde, quaternium-15, dimethyl-dimethyl (DMDM) hydantoin, imidazolidinyl urea, diazolidinyl urea, sodium hydroxymethylglycinate, and 2-bromo-2-nitropropane-1,3-diol;
3) Isothiazolones, such as chloromethyl-isothiozolinone (OMIT), methyl-isothiazolinone (MIT) or benz-isothiazolinone (BIT);
4) Halogen-organic actives, such as idopropynyl butylcarbamate and methyl-dibromo glutaranitrile;
5) Organic acids such as benzoic acid, dehydroacetic acid, salicylic acid, lactic acid and sorbic acids;
6) Other, including chloroacetamide, phenyloxyethanol and triclosan.

Additional suitable preservatives for personal care products can be found in "Preservatives for Cosmetics Manual, 2$^{nd}$ edition", by David S. Steinbens, 2006 and in "Preservatives for Cosmetics", D. C. Steinberg, Allured Publishing Corp., ISBN #0-93170-54-5. Such agents are typically employed at 0.1-1%, more preferably at 0.5-0.7% of the personal product formulation.

The organic acids noted are particularly preferred. Especially preferred are organic acids having pKa between about 4.0 and 5.5, preferably 4.0 and 5.0.

No preservative is ideal for all situations. For example, parabens are relatively non-irritant, but partition in favor of oil phase and are inactivated by some surfactants.

Formaldehyde-retaining preservatives have broad effectiveness spectrum, but are irritant and banned in some countries.

Applicants have filed a co-pending application directed to low pH based isotropic compositions having specific preservative systems.

Compositions of that application, and certainly compositions of this invention having preferred pH of about 3 to 5.1, preferably will comprise the organic acids noted above as preservative. Specifically, organic acids having pKa of 4.0 to 5.5, preferably 4.2 and 5.1 are preferred.

More specifically compositions preferably have pH which is less than one pH unit, more preferred less than 0.5 pH unit, above the pKa of the organic acid. Within such tight pH range, the organic acid will stay largely in undissociated form which is the form required for activity against microorganisms.

Thus, for example, since pKa of benzoic acid is 4.2, it is ideally suited to be used in composition of pH less than 5.2 (as in preferred embodiments of the invention), preferably at or less than 4.7.

As indicated, benzoic acid is a preferred preservative.

Optionally, the compositions of this invention may further comprise one or more additional ingredients. Non-limiting examples of such additional ingredients are, for example, colorants, pigments, opacifiers, fragrance (whether encapsulated or present as free-fragrance), emotive oils, vitamins and vitamin derivatives, abrasives, optical agents (including for example, reflective particles and interference pigments), pH adjusters, plant extracts, essential oils, preservatives, antioxidants, antimicrobials, viscosity modifiers, humectants, beard wetting agents, sensory agents, fatty acid soap, and skin and/or hair benefit agents (e.g., aloe, allantoin, panthenol, alpha-hydroxy acids, phospholipids, botanical oils, and amino acids to name a few). The selection and amount of any individual additional ingredient depends upon factors that include the particular ingredient, the properties desired, and the intended use of the composition in which it is employed. For example, fragrance is typically employed in an amount of 0.1 to 3.0% by weight of the composition, or higher. For many compositions, the total amount of such additional ingredients is 0.01 to 30% by weight, more particularly, 0.1 to 15% by weight, even more particularly, 1 to 10% by weight, based on the total weight of the composition.

In one or more embodiments, the total amount of such additional optional ingredients is 0.5 to 5% by weight. Other ingredients, for example fatty acid soap, may be present at levels up to 10% by weight, based on the total weight of the composition.

Compositions are aqueous based and comprise typically 30-90% by wt. water. Water is balance after all ingredients noted above are accounted for.

Protocols

Clarity

Transparency (clarity) of a sample is measured by measuring the optical absorbance at wavelength of $\lambda=550$ nm. The fully formulated samples (about 300 µl) are added into a 96-well plate without dilution and read by a microplate Reader (SpectraMax® 340PC, Molecular Device). An ideally transparent sample has zero absorbance (i.e., 100% transmission). In this invention, a sample with absorbance of below 1.5, more preferably below 1, more preferably below 0.5, even more preferably below 0.2 is defined as giving visually acceptable transparency (clarity).

EXAMPLES

Demonstration systems were constructed by weighing in predetermined masses of surfactants into a tared beaker. Applicants prepared example systems on a 50 g scale at 15% total surfactant. The desired blend of glutamate surfactants were weighed in first, followed by any co-surfactant. The total level of surfactant and co-surfactant was always 7.5 g. Then a charge of citric acid was added, calculated to be sufficient to yield a final pH of about 4.5. The system was then made up to 50 g with water and heated with stirring to 75° C. After 5-15 minutes of stirring, the resulting single phase, isotropic system was removed from the heat and allowed to cool to room temperature. Once cool, the pH was fine-tuned to pH 4.5 with 50% citric acid solution and water added to replace any lost during heating. Systems were equilibrated for two weeks at room temperature before making the observations used in constructing the phase maps.

In order to demonstrate compositions comprising surfactant system wherein glutamate is primary surfactant, applicants made various systems comprising (1) mixtures of $C_{10}/C_{12}$ glutamate and amphoacetate; (2) mixtures of $C_{10}/C_{coco}$ glutamate and amphoacetate; (3) mixtures of $C_{10}/C_{coco}$ glutamate and cocoamido propylbetaine (CAPB); (4) mixtures of $C_{10}/C_{coco}$ glutamate and cocoamidopropyl hydroxyl sultaine (CAPHS); and (5) mixtures of $C_{10}/C_{coco}$ glutamate and coco betaine.

Results are set forth as noted below.

Example 1

Stability Map of the lauroyl glutamate/amphoacetate system for 15% total surfactant and pH 4.5. Lauroyl glutamate was mixed with decanoyl glutamate as indicated. Symbol I=isotropic system with absorbance value at 550 nm below 0.2, X=two-phase system. In these systems, the left column represents % of $C_{10}$ relative to % of $C_{10}$ and $C_{12}$ so that, for example, 75 represents a system in which 75% of the total glutamate present is $C_{10}$ and 25% is $C_{12}$. The top row is % of amphoacetate with the balance being glutamate. Thus, 12.5 represents a system in which 87.5% of the surfactant is glutamate blend and 12.5% is amphoacetate. The total surfactant present is 15% in all cases, with the remainder being water with a minor amount of citric acid.

TABLE 1

| % decanoyl glutamate | % Na lauroamphoacetate | | | | |
|---|---|---|---|---|---|
| $[C_{10}/(C_{10} + C_{12})] \times 100$ | 0 | 12.5 | 25 | 37.5 | 50 |
| 100 | I | I | I | I | I |
| 75 | I | I | I | I | I |
| 50 | X | X | X | I | I |
| 25 | X | X | X | I | I |
| 0 | X | X | X | X | X |

It will be seen that, for this example, preferred stable, isotropic compositions are those with a ratio of $C_{10}/C_{12}$ acyl glutamate of about 1/3 and higher and with a ratio of lauroamphoacetate/acyl glutamate of about 1/1.7 and higher (up to 1/1). To ensure good foam performance and minimize costs, the ratio of $C_{10}/C_{12}$ acyl glutamate should be 1/1 and lower (preferably above 1/3) and the ratio of lauroamphoacetate/acyl glutamate should be 1/1 or lower.

Example 2

Stability Map of the cocoyl glutamate/amphoacetate system for 15% total surfactant and pH 4.5. Cocoyl glutamate was mixed with decanoyl glutamate as indicated. Symbol I=isotropic system with absorbance value at 550 nm below 0.2, X=two-phase system. Percentages are measured as noted in Table 1 of Example 1.

TABLE 2

| % decanoyl glutamate | % Na lauroamphoacetate | | | | |
|---|---|---|---|---|---|
| $[C_{10}/(C_{10} + C_{coco})] \times 100$ | 0 | 12.5 | 25 | 37.5 | 50 |
| 50 | I | I | I | I | X |
| 37.5 | I | I | I | I | X |
| 25 | X | I | I | I | X |
| 0 | X | X | I | I | I |

It will be seen that preferred stable, isotropic compositions are those with a ratio of $C_{10}/C_{coco}$ acyl glutamate of about 1/3 and higher and with a ratio of lauroamphoacetate/acyl glutamate of about 1/7 and higher. To ensure good foam performance, minimize costs, and observe an enhanced viscosity, the ratio of $C_{10}/C_{coco}$ acyl glutamate should be 1/1 and lower (preferably about 1/3 and above) and the ratio of lauroamphoacetate/acyl glutamate should be 1/1.7 or lower.

Example 3

Stability Map of the cocoyl glutamate/CAPB system for 15% total surfactant and pH 4.5. Cocoyl glutamate was mixed with decanoyl glutamate as indicated. Symbol I = isotropic system with absorbance value at 550 nm below 0.2, X=two-phase system. Percentages are measured as noted in Table 1.

TABLE 3

| % decanoyl glutamate | % CAPB | | | | |
|---|---|---|---|---|---|
| $[C_{10}/(C_{10} + C_{coco})] \times 100$ | 0 | 12.5 | 25 | 37.5 | 50 |
| 50 | I | I | X | X | X |
| 37.5 | I | X | X | X | X |
| 25 | X | X | X | X | X |
| 0 | X | X | X | X | X |

As seen from Examples 1-3, when we use a mixture of $C_{10}$ and $C_{coco}$, (Table 2) compared to mixture of $C_{10}$ and $C_{12}$ (Table 1), an isotropic region is achieved using lower amounts of $C_{10}$ glutamate. That is, less $C_{10}$ is needed to achieve soluble region (which also helps with lather production). Systems are glutamate plus co-surfactant (e.g., amphoacetate or cocoamidopropylbetaine). Non-ionic surfactant is a preferred co-surfactant in a glutamate/co-surfactant system. When co-surfactant used is CAPB rather than amphoacetate (Table 3 versus Table 2), some solubility benefit at lesser level of $C_{10}$ is lost. Even where solubility is lost, however, benefits of low pH (for alternative preservation systems) and foam from using high glutamate surfactant chassis are retained.

Example 4

Stability Map of the cocoyl glutamate/cocoamidopropyl hydroxyl sultaine (CAPHS) system for 15% total surfactant and pH 4.5. Cocoyl glutamate was mixed with decanoyl glutamate as indicated. Symbol I =isotropic system with absorbance value at 550 nm below 0.2, X=two phase system. Percentages are measured as noted in Table 1.

TABLE 4

| % decanoyl glutamate | | % CAPHS | | | | |
|---|---|---|---|---|---|---|
| $[C_{10}/(C_{10} + C_{coco})] \times 100$ | 0 | 5 | 12.5 | 25 | 37.5 | 50 |
| 50 | I | I | I | I | I | I |
| 37.5 | I | I | I | I | I | I |
| 25 | X | I | I | I | I | I |
| 0 | X | X | X | X | I | I |

It will be seen that preferred stable, isotropic compositions are those with a ratio of $C_{10}/C_{coco}$ acyl glutamate (using CAPHS, less co-surfactant is needed to obtain isotropic region compared to certain other co-surfactants, e.g., CAPB or amphoacetate) of about 1/7 and higher and with a ratio of CAPHS/acyl glutamate of about 1/19 and higher. To ensure good foam performance, minimize costs, and observe an enhanced viscosity, the ratio of $C_{10}/C_{coco}$ acyl glutamate should be 1/1 and lower and the ratio of CAPHS/acyl glutamate should be 1/1 or lower.

Example 5

Stability Map of the cocoyl glutamate/coco betaine system for 15% total surfactant and pH 4.5. Cocoyl glutamate was mixed with decanoyl glutamate as indicated. Symbol I—isotropic system with absorbance value at 550 nm below 0.2, X=two phase system. Percentages are measured as noted in Table 1.

TABLE 5

| % decanoyl glutamate | | % cocoyl betaine | | | | |
|---|---|---|---|---|---|---|
| $[C_{10}/(C_{10} + C_{coco})] \times 100$ | 0 | 5 | 12.5 | 25 | 37.5 | 50 |
| 50 | I | I | I | I | I | I |
| 37.5 | I | I | I | I | I | I |
| 25 | X | I | I | I | I | I |
| 0 | X | X | I | I | I | I |

It will be seen that preferred stable, isotropic compositions are those with a ratio of $C_{10}/C_{coco}$ acyl glutamate of about 1/7 and higher and with a ratio of coco betaine/acyl glutamate of about 1/19 and higher (less co-surfactant needed to obtain isotropic regions compared to use of certain other co-surfactants). To ensure good foam performance, minimize costs, and observe an enhanced viscosity, the ratio of $C_{10}/C_{coco}$ acyl glutamate should be 1/1 and lower and the ratio of coco betaine/acyl glutamate should be 1/1 or lower.

As seen from Examples 2, 4 and 5, when we use a mixture of $C_{10}$ and $C_{coco}$ glutamates along with a co-surfactant chosen from the preferred list of amphoteric surfactants, a broad, isotropic, stable region results. More specifically, blending shorter chain length glutamates (decanoyl glutamate) with longer chain length glutamates (cocoyl glutamate) yields isotropic systems at pH 4.5 in which glutamate comprises 100% of the surfactant system. Further, addition of preferred amphoteric co-surfactants to glutamate blends results in isotropic systems in which glutamate comprise ≥50% of the surfactant system and 100% of the total anionic surfactant while allowing for a glutamate blend richer in longer chain lengths, which enhances foaming. Again, even where benefit agents in final system may form anisotropic compositions, foam benefits are retained.

Examples 6-8

For Examples 6-8, finished formulations were prepared by adding the surfactants, starch, and 70% of the free water into a tared vessel immersed in a water bath and with overhead mixing. The components are stirred until uniformly mixed and then the stirring continued as the water bath temperature is raised to 70° C. Once at temperature, the Jaguar (predispersed in glycerin) and PEG are added along with the citric acid. Cooling is initiated and the other components added once the water bath reaches 35° C. The final pH and water content are then adjusted.

| Chemical/ Trade Name | % active as supplied | Example 6 % on 100% active basis | Example 7 % on 100% active basis | Example 8 % on 100% active basis |
|---|---|---|---|---|
| Water | 100 | 84.27 | 83.85 | 79.35 |
| Puregel B990 (modified starch; thickener) | 100 | 0.00 | 0.00 | 4.5 |
| Lauroyl Glutamate | 100 | 6.60 | 6.60 | 0.00 |
| Cocoyl Glutamate | 100 | 0.00 | 0.00 | 6.60 |
| Na Lauroyl Sarcosinate | 30 | 0.00 | 0.00 | 0.00 |
| Sodium lauroamphoacetate | 20 | 5.40 | 5.40 | 5.40 |
| Jaguar C-14 | 100 | 0.3 | 0.3 | 0.3 |
| Glycerin | 100 | 2.00 | 2.00 | 2.00 |
| PEG-45M | 100 | 0.05 | 0.05 | 0.05 |
| Citric acid | 50 | 1.25 | 1.25 | 1.25 |
| Sodium benzoate (preservative) | 100 | 0.00 | 0.5 | 0.5 |
| butylated hydroxytoluene (BHT) | 100 | 0.00 | 0.00 | 0.00 |
| Methylisothiazolinone (MIT) (preservative) | 9.5 | 0.01 | 0.00 | 0.00 |
| Glydant Plus Liquid (preservative) | 20 | 0.07 | 0.00 | 0.00 |
| EDTA (ethylenediamine tetraacetic acid) (sequestrant) | 39 | 0.05 | 0.05 | 0.05 |
| Total | | 100 | 100 | 100 |
| pH | | 4.5 | 4.5 | 4.5 |

Example 6 is typical of a conventional preservation system, which can be used over a wide pH range but whose application is regionally restricted. In contrast, Example 7 illustrates a preservation system which is preferred in those regions but which will only function at pH 5.0 and below. The example formulation provides an effective product form in which to practice this preservation system. Both examples yielded stable, isotropic, single phase systems. Example 8 is an example of a finished formulation which contains optional benefiting ingredients (Puregel® B990 in this case, a starch thickening agent) which render the final system anisotropic, though still stable against physical phase separation.

Examples 9-11

For Examples 9-11, finished formulations were prepared as described for Examples 6-8.

| Chemical/ Trade Name | % active as supplied | Example 9 % on 100% active basis | Example 10 % on 100% active basis | Example 11 % on 100% active basis |
|---|---|---|---|---|
| Water | 100 | 77.99 | 74.75 | 64.44 |
| (modified polyacrylate; thickener)[1] | 34 | 0.5 | 0.5 | 0.0 |
| Puregel B990 (modified starch thickener) | 100 | 0.0 | 0.0 | 4.50 |
| Carbopol 980 | 100 | 0.0 | 0.0 | 0.6 |
| Decanoyl Glutamate | 100 | 4.39 | 4.39 | 0.0 |
| Cocoyl Glutamate | 23 | 4.39 | 4.39 | 6.6 |
| Na Lauroyl Sarcosinate | 30 | 0.95 | 0.95 | 0.0 |
| Cocamidopropyl hydroxy sultaine | 40 | 5.28 | 6.00 | 0.0 |
| Sodium lauroamphoacetate | 28 | 0.0 | 0.0 | 5.40 |
| Jaguar C-14 | 100 | 0.0 | 0.1 | 0.30 |
| Glycerin | 100 | 5.00 | 2.00 | 6.0 |
| PEG-14M | 100 | 0.0 | 0.0 | 0.5 |
| PEG-45M | 100 | 0.05 | 0.05 | 0.0 |
| Soybean Oil | 100 | 0.0 | 3.0 | 0.0 |
| Hydrogenated Soybean Oil | 100 | 0.0 | 2.0 | 0.0 |
| Petrolatum | 100 | 0.0 | 0.0 | 8.75 |
| Polybutene (H-300) | 100 | 0.0 | 0.0 | 0.5 |
| Citric acid | 50 | 1.32 | 1.32 | 1.15 |
| Sodium benzoate (preservative) | 100 | 0.00 | 0.5 | 0.0 |
| butylated hydroxytoluene (BHT) | 100 | 0.00 | 0.00 | 0.10 |
| Methylisothiazolinone (MIT) (preservative) | 9.5 | 0.01 | 0.00 | 0.01 |
| Glydant Plus Liquid (preservative) | 20 | 0.07 | 0.00 | 0.0 |
| EDTA (ethylenediamine tetraacetic acid) (sequestrant) | 39 | 0.05 | 0.05 | 0.05 |
| Fragrance | 100 | 0.0 | 0.0 | 1.10 |
| Total | | 100 | 100 | 100 |
| pH | | 4.8 | 4.8 | 4.8 |

[1]This is a copolymer which is the polymerization product of (by weight of total polymer) (a) about 40 to 70% ethyl acrylate; (b) 20 to 50% methacrylic acid; (c) 0.1 to 3% maleic anhydride and; (d) 2 to 15% of an associative monomer (for example, Component D of Formula V defined above).

Example 9 is typical of a conventional preservation system, which can be used over a wide pH range but whose application is regionally restricted. In contrast, Example 10 illustrates a preservation system which is preferred in those regions but which will only function at pH 5.0 and below. The example formulation provides an effective product form in which to practice the preservation system. Both examples yielded stable, isotropic, single phase surfactant chassis. Example 10 is an example of a finished formulation which contains optional benefiting ingredients (soybean oil and hydrogenated soybean oil in this case, an emollient oil) which render the final system anisotropic, though still stable against physical phase separation. Similarly, Example 11 is an example of a finished formulation which contains optional benefiting ingredients (petrolatum and polybutene, an emollient oil and sensory modifier, respectively) which render the final system anisotropic, though still stable against physical phase separation.

The invention claimed is:
1. Cleansing composition comprising:
   a) 0.5 to 35% by wt. total composition of a surfactant system comprising anionic surfactant comprising salt of acyl glutamate, wherein salt of acyl glutamate is present at 50 wt % or more of all surfactant present, and wherein the surfactant system further comprises 0 to 20% by wt. total composition of a co-surfactant, wherein co-surfactant are surfactants which are not anionic, selected from the group consisting of non-ionic, cationic, amphoteric surfactants and mixtures thereof;
   b) 0% to 30% by wt. total composition of a water-soluble or oil-soluble skin or hair benefit agent, not being a surfactant; and
   c) water
   wherein pH is 5.5 or lower, wherein
      salt of glutamate comprises a mixture of $C_{10}$ and $C_{coco}$ glutamate, wherein the mixture of $C_{10}$ and $C_{coco}$ has a $C_8$-$C_{10}$ chain length distribution wherein $C_8$-$C_{10}$ is present in an amount of more than 13%, or
      salt of glutamate comprises a mixture of $C_{10}$ and $C_{12}$ glutamate, wherein the ratio of $C_{10}$ to $C_{12}$ is at least 1/5,
   wherein the salt of glutamate has a cation which is sodium or potassium.
2. A composition according to claim 1, wherein the composition is clear, wherein clear is defined by absorbance value of 1.0 or below when measured at wavelength of 550 nm, adding 300 μl into a 96-well plate without dilution.
3. A composition according to claim 1, comprising 0.5 to 15% co-surfactant.
4. A composition according to claim 1, wherein co-surfactant comprises an amphoteric surfactant.
5. A composition according to claim 1 further comprising 0.1% to 5% by wt. benefit agent.
6. A composition according to claim 1 wherein said benefit agent is an oil-soluble emollient or moisturizing oil.
7. A composition according to claim 1 wherein pH of composition is 3.5 to 5.5.
8. A composition according to claim 7 wherein pH is 4.0 to 5.5.
9. A composition according to claim 8 wherein pH is 4 to 5.1.
10. A composition according to claim 1, additionally comprising structurant.
11. A composition according to claim 10 which comprises a structurant having formula:

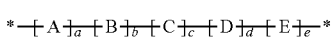

(I)

wherein a, b, c, d and e represent the percentage by weight that each repeating unit monomer is contained within the copolymer;

A is a polyacidic vinyl monomer selected from the group consisting of maleic, fumaric, itaconic, citraconic and acid combinations thereof and anhydrides and salts thereof; and B is acrylic or methacrylic acid or a salt thereof;

C is a $C_1$-$C_8$ ester of acrylic acid or methacrylic acid;

D is an associative monomer of formula (II)

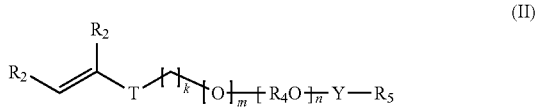

wherein each $R_2$ is independently H, methyl, —C(=O)OH, or —C(=O)$OR_3$;

$R_3$ is a $C_1$-$C_{30}$ alkyl;

T is —$CH_2$C(=O)O—, —C(=O)O—, —O—, —$CH_2$O—, —NHC(=O)NH—, —C(=O)NH—, —Ar—$(CF_2)_z$—NHC(=O)O—, —Ar—$(CF_2)_z$—NHC(=O)NH—, or —$CH_2CH_2$NHC(=O)—;

Ar is divalent aryl;

F is H or methyl;

z is 0 or 1;

k is an integer in the range of 0 to 30; and m is 0 or 1; with the proviso that when k is 0, m is 0, and when k is in the range of 1 to 30; m is 1;

$(R_4O)_n$ is polyoxyalkylene, which is a homopolymer, a random copolymer, or a block copolymer of $C_2$-$C_4$-oxyalkylene units, wherein $R_4$ is $C_2H_4$, $C_3H_6$, $C_4H_8$, or a mixture thereof, and n is an integer in the range of 5 to 250;

Y is —$R_4$O—, —$R_4$H—, —C(=O)—, —C(=O)NH—, =$R_4$NHC(=O)NH—, or —C(=O)NHC(=O)—; and $R_5$ is substituted or unsubstituted alkyl selected from the group consisting of $C_8$-$C_{40}$ linear alkyl, $C_8$-$C_{40}$ branched alkyl, $C_8$-$C_{40}$ carbocyclic alkyl, $C_2$-$C_{40}$ alkyl-substituted, phenyl, aryl-substituted $C_2$-$C_{40}$ alkyl, and $C_8$-$C_{80}$ complex ester; wherein the $R_5$ alkyl group optionally comprises one or more substituents selected from the group consisting of hydroxy, alkoxy, and halogen; and E when present is a cross linking monomer for introducing branching and controlling molecular weight, the cross linking monomer comprising polyfunctional units carrying multiple reactive functionalization groups selected from the group consisting of vinyl, allylic and functional mixtures thereof, the groups A, B, C, D and E being covalently bonded one to another in a manner selected from a random, a block or a cross-linked copolymer format.

12. A composition according to claim 1 further comprising immiscible benefit agent.

13. A composition according to claim 1 wherein salt of acyl glutamate is selected from the group consisting of $C_{10}$, $C_{12}$ and $C_{coco}$ glutamate and mixtures thereof, co-surfactant is amphoacetate and ratio of amphoacetate to salt of glutamate is 1/7 and higher.

14. A composition according to claim 13, wherein ratio is 1/7 to 1/1.

15. A composition according to claim 1, wherein salt of glutamate is selected from the group consisting of $C_{10}$, $C_{12}$ and $C_{coco}$ glutamate and mixtures thereof, co-surfactant is selected from the group consisting of betaine, sultaine and mixtures thereof and ratio of co-surfactant to glutamate of 1/19 and higher.

16. A composition according to claim 15, wherein ratio is 1/19 to 1/1.

\* \* \* \* \*